(12) United States Patent
Hirose

(10) Patent No.: US 11,606,505 B2
(45) Date of Patent: Mar. 14, 2023

(54) MEDICAL OBSERVATION APPARATUS AND MEDICAL OBSERVATION SYSTEM

(71) Applicant: Sony Olympus Medical Solutions Inc., Tokyo (JP)

(72) Inventor: Kenji Hirose, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 497 days.

(21) Appl. No.: 16/724,789

(22) Filed: Dec. 23, 2019

(65) Prior Publication Data

US 2020/0288064 A1 Sep. 10, 2020

(30) Foreign Application Priority Data

Mar. 7, 2019 (JP) .............................. JP2019-041593

(51) Int. Cl.
*H04N 5/232* (2006.01)
*B25J 9/16* (2006.01)
*A61B 90/00* (2016.01)
*A61B 90/25* (2016.01)

(52) U.S. Cl.
CPC ......... *H04N 5/23299* (2018.08); *A61B 90/25* (2016.02); *A61B 90/361* (2016.02); *B25J 9/1697* (2013.01); *H04N 5/23203* (2013.01)

(58) Field of Classification Search
CPC ............ H04N 5/2251; H04N 5/23299; H04N 5/23296; H04N 5/232; A61B 90/20; A61B 90/361; A61B 90/25; A61B 2090/508; A61B 90/50; A61B 90/30; A61B 2090/506; A61B 2090/3616; A61B 2090/371; A61B 2034/2059; B25J 9/1697
See application file for complete search history.

(56) References Cited

U.S. PATENT DOCUMENTS

| 10,849,484 B2* | 12/2020 | Shioda | G02B 27/017 |
| 11,160,633 B2* | 11/2021 | Tamura | G02B 21/0012 |
| 2017/0176704 A1* | 6/2017 | Hirose | H04N 5/23296 |
| 2017/0343792 A1* | 11/2017 | Matsunobu | A61N 5/0603 |

FOREIGN PATENT DOCUMENTS

| JP | 05-253245 A | 10/1993 |
| JP | 2001145634 A | 5/2001 |
| JP | 2005118457 A | 5/2005 |
| JP | 2017176307 A | 10/2017 |
| JP | 2018064951 A | 4/2018 |
| JP | 2018-81315 A | 5/2018 |
| WO | WO-2018049448 A2 | 3/2018 |

\* cited by examiner

*Primary Examiner* — Tsion B Owens
(74) *Attorney, Agent, or Firm* — Xsensus LLP

(57) ABSTRACT

A medical observation apparatus includes: a camera configured to capture an object image of an observation target; a support configured to support the camera so as to be rotatable about a plurality of mutually-different shafts; a memory configured to store the position of the camera; a brake configured to switch between: a permission state for permitting the camera to rotate about at least one of the plurality of shafts; and a restriction state for restricting the rotation; and a controller configured to perform a reproduction process for switching the brake to the permission state, and thereafter switching the brake from the permission state to the restriction state when the support is operated according to an external force applied to the support by an operator and the camera is located at the position of the camera stored in the memory.

20 Claims, 13 Drawing Sheets

MEDICAL OBSERVATION APPARATUS AND MEDICAL OBSERVATION SYSTEM

This application claims priority from Japanese Application No. 2019-041593, filed on Mar. 7, 2019, the contents of which are incorporated by reference herein in its entirety.

BACKGROUND

The present disclosure relates to a medical observation apparatus and a medical observation system.

There are a known medical observation apparatus including an imaging unit that magnifies and captures a minute part of an operative site of a patient, and a support unit that supports the imaging unit so as to be rotatable about a plurality of mutually-different shafts (For example, see JP 2018-81315 A).

In the support unit disclosed in JP 2018-81315 A, all the shafts are each constituted by a passive shaft capable of passively rotating the imaging unit about the shaft according to an external force applied to the support unit by an operator, such as a surgeon, without the power of an actuator or the like. That is, in the support unit disclosed in JP 2018-81315 A, all the shafts are not provided with actuators. Furthermore, in the support unit disclosed in JP 2018-81315 A, all the shafts are not provided with angle sensors that detect rotation angles about the respective shafts.

In addition, as a support unit (a motor-driven frame) having a structure different from the support unit disclosed in JP 2018-81315 A, there is a known configuration in which all the shafts are constituted by active shafts capable of actively rotating an imaging unit (a therapeutic and diagnostic instrument) about the respective shaft with the power of an actuator (see, for example, JP H05-253245 A). That is, in the support unit disclosed in JP H05-253245 A, all the shafts are provided with actuators. Furthermore, in the support unit disclosed in JP H05-253245 A, all the shafts are provided with angle sensors that detect rotation angles about the respective shafts.

SUMMARY

In recent years, for the purpose of grasping the condition of an operative site after a treatment (surgery), a technique for analyzing changes in blood flow in the operative site by comparing a captured image obtained by imaging the operative site before the treatment and a captured image obtained by imaging the operative site after the treatment (hereinafter, referred to as an analysis method) has been developed. In this analysis method, it is necessary to capture an operative site under the same conditions before and after a treatment. That is, in order to perform the analysis method using the medical observation apparatus disclosed in JP 2018-81315 A, it is necessary for the imaging unit to perform imaging before and after a treatment at the same position.

However, there are problems described below in performing the analysis method using the medical observation apparatus disclosed in JP 2018-81315 A.

That is, in order to reproduce, after the treatment, the position of the imaging unit at which the imaging unit have performed imaging before the treatment (hereinafter, referred to as a pre-treatment position), an operator is required to manually operate the support unit so that a captured image currently captured looks the same as the captured image captured before the treatment while checking the currently-captured image displayed on a display device. For this reason, it takes a long time to reproduce the position of the imaging unit at the pre-treatment position, and it is difficult to accurately reproduce the position of the imaging unit at the pre-treatment position.

On the other hand, in the support unit disclosed in JP H05-253245 A, all the shafts are provided with actuators and angle sensors. For this reason, when the above analysis method is performed by mounting the support unit disclosed in JP H05-253245 A in the medical observation apparatus disclosed in JP 2018-81315 A and using this medical observation apparatus, the position of the imaging unit may be automatically reproduced at the pre-treatment position using the operation of the actuators as long as the pre-treatment position is stored in a storage unit or the like, and convenience may be improved.

However, since all the shafts are provided with actuators in the support unit disclosed in JP H05-253245 A, the cost is increased.

According to one aspect of the present disclosure, there is provided a medical observation apparatus including: a camera configured to capture an object image of an observation target; a support configured to support the camera so as to be rotatable about a plurality of mutually-different shafts; a memory configured to store the position of the camera; a brake configured to switch between: a permission state for permitting the camera to rotate about at least one of the plurality of shafts; and a restriction state for restricting the rotation; and a controller configured to perform a reproduction process for switching the brake to the permission state, and thereafter switching the brake from the permission state to the restriction state when the support is operated according to an external force applied to the support by an operator and the camera is located at the position of the camera stored in the memory.

DETAILED DESCRIPTION

Hereinafter, modes for carrying out the present disclosure (hereinafter, embodiments) will be described with reference to the drawings. Note that, the present disclosure is not limited to the embodiments described below. Furthermore, the same elements are denoted by the same reference signs in the description of the drawings.

First Embodiment

Schematic Configuration of Medical Observation System

Figure 1:
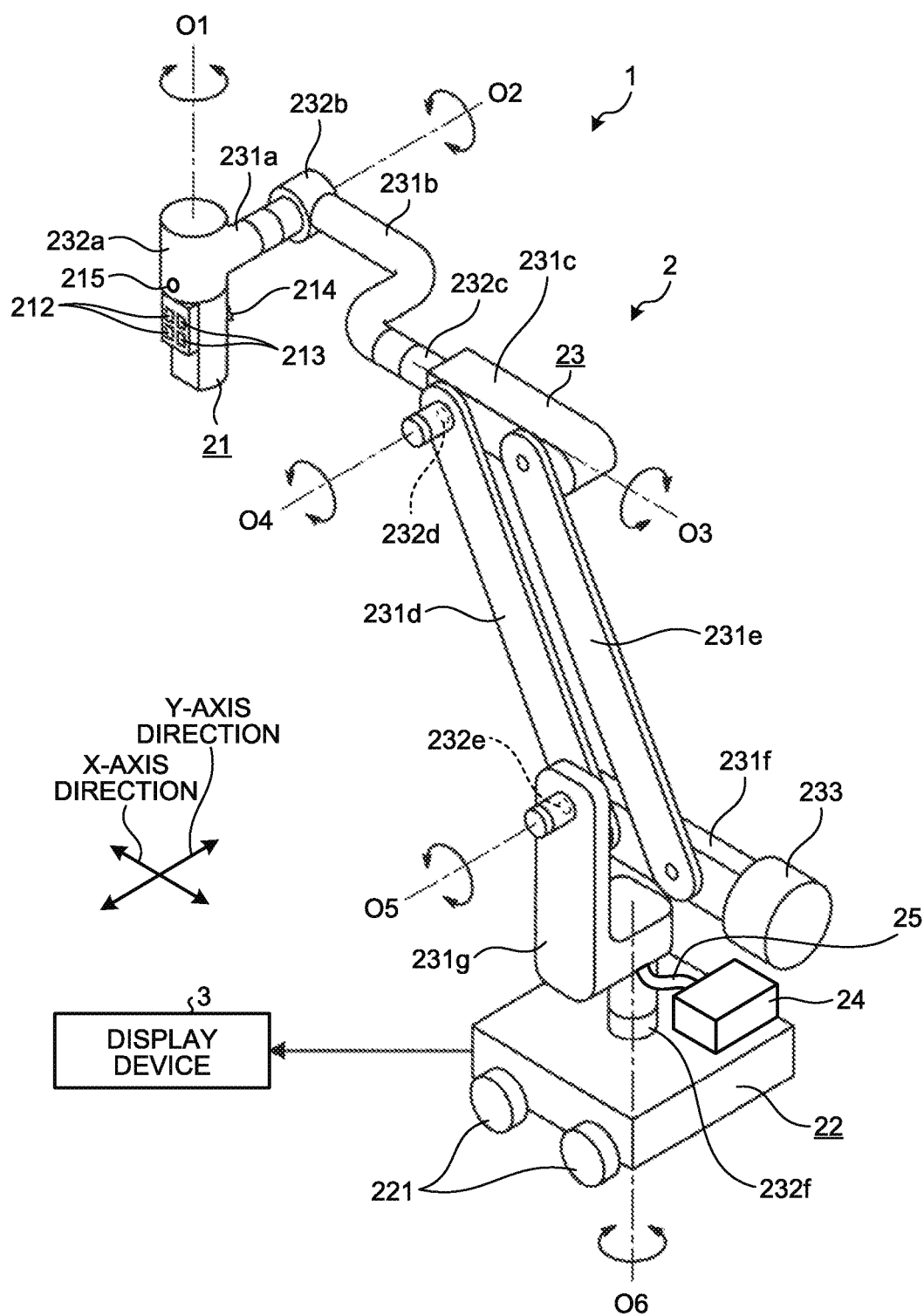
FIG. 1 is a diagram illustrating a medical observation system according to a first embodiment.
Figure 2:
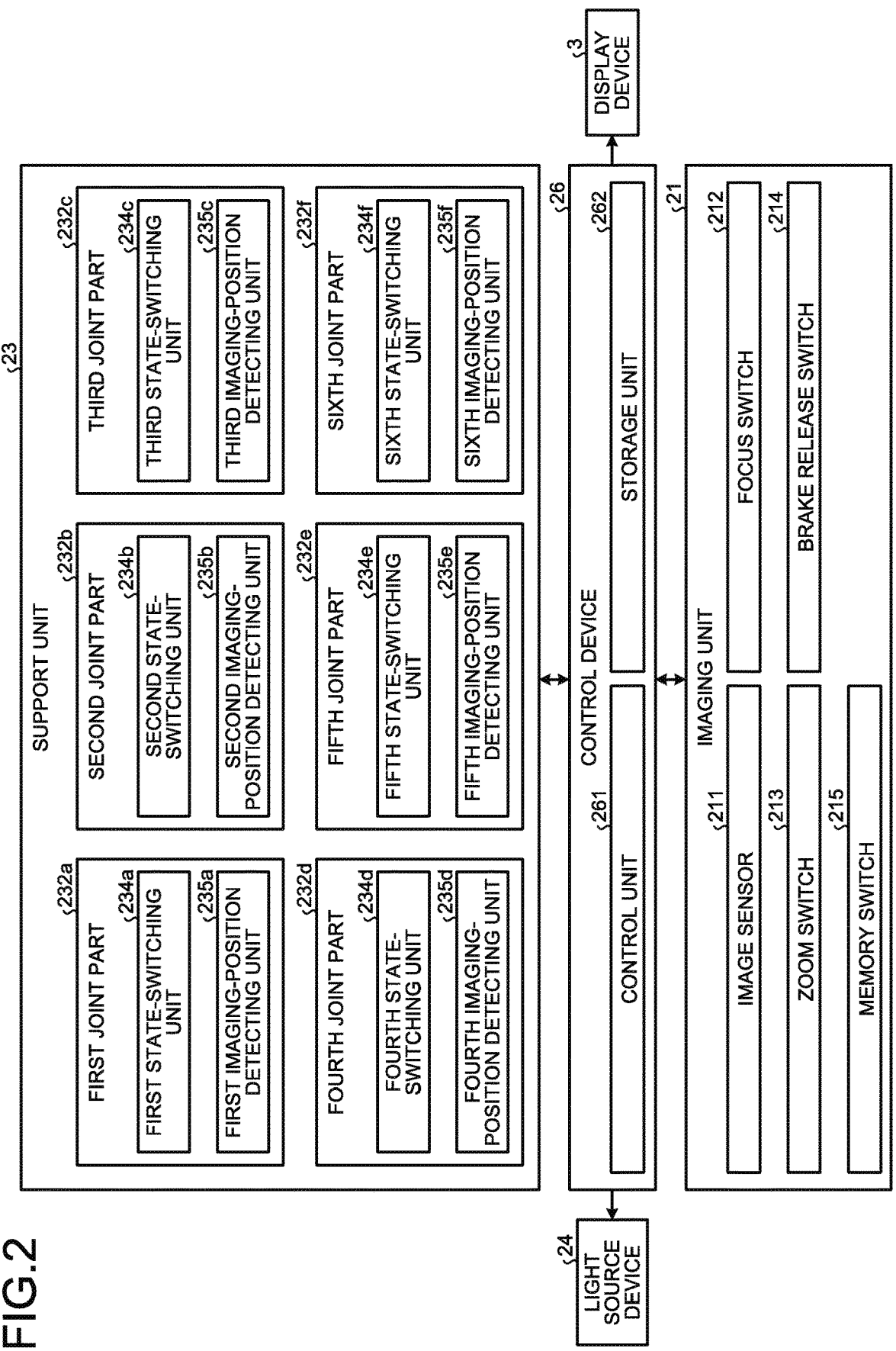
FIG. 2 is a block diagram illustrating a configuration of a control device.

FIG. 1 is a diagram illustrating a medical observation system 1 according to a first embodiment. FIG. 2 is a block diagram illustrating a configuration of a control device 26.

The medical observation system 1 is a system for capturing an object image of an observation target and for displaying a captured imaged obtained by the imaging, in order to, for example, support microsurgery, such as neurosurgical operation, or to perform endoscopic surgery. As illustrated in FIG. 1, the medical observation system 1 includes a medical observation apparatus 2 that captures an object image of an observation target, and a display device 3 that displays a captured image obtained by imaging of the medical observation apparatus 2.

As illustrated in FIG. 1 or 2, the medical observation apparatus 2 includes an imaging unit 21, a base unit 22 (FIG. 1), a support unit 23, a light source device 24, a light guide 25 (FIG. 1), and a control device 26 (FIG. 2).

The imaging unit 21 includes a lens unit (not illustrated) and an image sensor 211 (FIG. 2).

The lens unit includes a focus optical system and a zoom optical system, captures an object image of an observation target, and forms the image on the imaging surface of the image sensor 211.

The image sensor 211 is constituted by a charge coupled device (CCD) sensor, a complementary metal-oxide-semiconductor (CMOS) sensor, or the like that receives the object image formed by the lens unit and converts it into an electrical signal. The image sensor 211 captures the object image of the observation target under the imaging conditions (the shutter speed, sensitivity, gain, and the like) designated by the control device 26.

The imaging unit 21 further adjusts, under the control of the control device 26, the focus (the focal length to the observation target) according to an operation of an operator, such as a surgeon, to a focus switch 212 (FIGS. 1 and 2) provided on the imaging unit 21. The imaging unit 21 further adjusts, under the control of the control device 26, the field angle (the magnification ratio of the observation target) according to an operation of the operator to a zoom switch 213 (FIGS. 1 and 2) provided on the imaging unit 21. Note that, the imaging unit 21 may be configured as what is called a stereo camera by providing two image sensors 211.

The base unit 22 is a base of the medical observation apparatus 2, and is configured to be movable on the floor surface via casters 221 (FIG. 1).

The support unit 23 extends from the base unit 22 and supports the imaging unit 21 at the distal end (an end away from the base unit 22). The support unit 23 enables the imaging unit 21 to move three-dimensionally according to an external force applied by the operator.

In the first embodiment, the support unit 23 is configured to have six degrees of freedom with respect to the movement of the imaging unit 21, but is not limited thereto, and may be configured to have different degrees of freedom.

As illustrated in FIG. 1, the support unit 23 includes first to seventh arm parts 231*a* to 231*g* and first to sixth joint parts 232*a* to 232*f*.

The first joint part 232*a* is positioned at the distal end of the support unit 23. The first joint part 232*a* holds the imaging unit 21 so as to be rotatable about a first axis O1 (FIG. 1) while being fixedly supported by the first arm part 231*a*.

Here, the first axis O1 aligns with the observation optical axis of the imaging unit 21. That is, when the imaging unit 21 is rotated about the first axis O1, the direction of the imaging field of the imaging unit 21 is changed.

The first arm part 231*a* is a substantially rod-like member extending in a direction orthogonal to the first axis O1, and fixedly supports the first joint part 232*a* at the distal end.

The second joint part 232*b* holds the first arm part 231*a* so as to be rotatable about a second axis O2 (FIG. 1) while being fixedly supported by the second arm part 231*b*. Thus, the second joint part 232*b* enables the imaging unit 21 to rotate about the second axis O2.

Here, the second axis O2 is orthogonal to the first axis O1, and is parallel to the extending direction of the first arm part 231*a*. That is, when the imaging unit 21 is rotated about the second axis O2, the direction of the optical axis of the imaging unit 21 with respect to the observation target is changed. In other words, the imaging field of the imaging unit 21 moves along an X axis (FIG. 1) orthogonal to the first and second axes O1 and O2 in the horizontal plane. Thus, the second joint part 232*b* is a joint part for moving the imaging field of the imaging unit 21 along the X axis.

The second arm part 231*b* has a crank shape extending in a direction orthogonal to the first and second axes O1 and O2, and fixedly supports the second joint part 232*b* at the distal end.

The third joint part 232*c* holds the second arm part 231*b* so as to be rotatable about a third axis O3 (FIG. 1) while being fixedly supported by the third arm part 231*c*. Thus, the third joint part 232*c* enables the imaging unit 21 to rotate about the third axis O3.

Here, the third axis O3 is orthogonal to the first and second axes O1 and O2. That is, when the imaging unit 21 is rotated about the third axis O3, the direction of the optical axis of the imaging unit 21 with respect to the observation target is changed. In other words, the imaging field of the imaging unit 21 moves along the Y axis (FIG. 1) orthogonal to the X axis in the horizontal plane. Thus, the third joint part 232*c* is a joint part for moving the imaging field of the imaging unit 21 along the Y axis.

The third arm part 231*c* is a substantially rod-like member extending in a direction substantially parallel to the third axis O3, and fixedly supports the third joint part 232*c* at the distal end.

The fourth joint part 232*d* holds the third arm part 231*c* so as to be rotatable about a fourth axis O4 (FIG. 1) while being fixedly supported by the fourth arm part 231*d*. Thus, the fourth joint part 232*d* enables the imaging unit 21 to rotate about the fourth axis O4.

Here, the fourth axis O4 is orthogonal to the third axis O3. That is, when the imaging unit 21 is rotated about the fourth axis O4, the height of the imaging unit 21 is adjusted. Thus, the fourth joint part 232*d* is a joint part for moving the imaging unit 21 in parallel.

The fourth arm part 231*d* is a substantially rod-like member orthogonal to the fourth axis O4 and linearly extending toward the base unit 22, and fixedly supports the fourth joint part 232*d* at one end.

The fifth arm part 231*e* has the same shape as the fourth arm part 231*d*. The fifth arm part 231*e* is coupled to the third arm part 231*c* so that one end thereof is rotatable about an axis parallel to the fourth axis O4.

The sixth arm part 231*f* has substantially the same shape as the third arm part 231*c*. The sixth arm part 231*f* is coupled to the other ends of the fourth and fifth arm parts 231d and 231e so as to be rotatable about an axis parallel to the fourth axis O4 while forming a parallelogram together with the third to fifth arm parts 231c to 231e. A counterweight 233 (FIG. 1) is provided at an end of the sixth arm part 231f.

The mass and the arrangement position of the counterweight 233 are adjusted so that the rotational moment about the fourth axis O4 and the rotational moment about the fifth axis O5 (FIG. 1) that are generated due to the mass of the components provided closer to the distal end of the support unit 23 (the position at which the imaging unit 21 is provided) than the counterweight 233 may be canceled. That is, the support unit 23 is a balance arm (provided with the counterweight 233). Note that, the support unit 23 may not be provided with the counterweight 233.

The fifth joint part 232e holds the fourth arm part 231d so as to be rotatable about a fifth axis O5 while being fixedly supported by the seventh arm part 231g. Thus, the fifth joint part 232e enables the imaging unit 21 to rotate about the fifth axis O5.

Here, the fifth axis O5 is parallel to the fourth axis O4. That is, when the imaging unit 21 is rotated about the fifth axis O5, the height of the imaging unit 21 is adjusted. Thus, the fifth joint part 232e is a joint part for moving the imaging unit 21 in parallel.

The seventh arm part 231g has a substantially L-shape constituted by a first portion extending in the vertical direction and a second portion extending by bending substantially orthogonal to the first portion, and fixedly supports the fifth joint part 232e at the first portion.

The sixth joint part 232f holds the second portion of the seventh arm part 231g so as to be rotatable about a sixth axis O6 (FIG. 1) while being fixedly supported by the base unit 22. Thus, the sixth joint part 232f enables the imaging unit 21 to rotate about the sixth axis O6.

Here, the sixth axis O6 is an axis along the vertical direction. Thus, the sixth joint part 232f is a joint part for moving the imaging unit 21 in parallel.

The first to sixth axes O1 to O6 described above correspond to respective shafts according to the present disclosure. In addition, the first axis O1 is constituted by a passive shaft capable of passively rotating the imaging unit 21 about the first axis O1 according to an external force applied by the operator without the power of an actuator or the like. Similarly, the second to sixth axes O2 to O6 are each constituted by a passive shaft. Furthermore, as illustrated in FIG. 2, the first to sixth joint parts 232a to 232f respectively include first to sixth state-switching units 234a to 234f each constituted by an electromagnetic brake or the like, and first to sixth imaging-position detecting units 235a to 235f each constituted by a rotary encoder, an angular velocity sensor, or the like. Here, the first to sixth state-switching units 234a to 234f correspond to respective state-switching units according to the present disclosure. The first to sixth imaging-position detecting units 235a to 235f correspond to respective imaging-position detecting units according to the present disclosure.

The first state-switching unit 234a switches, under the control of the control device 26, to either a permission state for permitting the imaging unit 21 to rotate about the first axis O1 or a restriction state for restrict the rotation.

The second state-switching unit 234b switches, under the control of the control device 26, to either a permission state for permitting the imaging unit 21 to rotate about the second axis O2 or a restriction state for restrict the rotation.

The third state-switching unit 234c switches, under the control of the control device 26, to either a permission state for permitting the imaging unit 21 to rotate about the third axis O3 or a restriction state for restrict the rotation.

The fourth state-switching unit 234d switches, under the control of the control device 26, to either a permission state for permitting the imaging unit 21 to rotate about the fourth axis O4 or a restriction state for restrict the rotation.

The fifth state-switching unit 234e switches, under the control of the control device 26, to either a permission state for permitting the imaging unit 21 to rotate about the fifth axis O5 or a restriction state for restrict the rotation.

The sixth state-switching unit 234f switches, under the control of the control device 26, to either a permission state for permitting the imaging unit 21 to rotate about the sixth axis O6 or a restriction state for restrict the rotation.

The first imaging-position detecting unit 235a detects, under the control of the control device 26, the rotation angle of the imaging unit 21 (the position of the imaging unit 21) rotating about the first axis O1. Then, the first imaging-position detecting unit 235a outputs a signal corresponding to the detected rotation angle to the control device 26.

The second imaging-position detecting unit 235b detects, under the control of the control device 26, the rotation angle of the imaging unit 21 (the position of the imaging unit 21) rotating about the second axis O2. Then, the second imaging-position detecting unit 235b outputs a signal corresponding to the detected rotation angle to the control device 26.

The third imaging-position detecting unit 235c detects, under the control of the control device 26, the rotation angle of the imaging unit 21 (the position of the imaging unit 21) rotating about the third axis O3. Then, the third imaging-position detecting unit 235c outputs a signal corresponding to the detected rotation angle to the control device 26.

The fourth imaging-position detecting unit 235d detects, under the control of the control device 26, the rotation angle of the imaging unit 21 (the position of the imaging unit 21) rotating about the fourth axis O4. Then, the fourth imaging-position detecting unit 235d outputs a signal corresponding to the detected rotation angle to the control device 26.

The fifth imaging-position detecting unit 235e detects, under the control of the control device 26, the rotation angle of the imaging unit 21 (the position of the imaging unit 21) rotating about the fifth axis O5. Then, the fifth imaging-position detecting unit 235e outputs a signal corresponding to the detected rotation angle to the control device 26.

The sixth imaging-position detecting unit 235f detects, under the control of the control device 26, the rotation angle of the imaging unit 21 (the position of the imaging unit 21) rotating about the sixth axis O6. Then, the sixth imaging-position detecting unit 235f outputs a signal corresponding to the detected rotation angle to the control device 26.

The light source device 24 is connected to one end of the light guide 25, and supplies illumination light with a light amount designated by the control device 26 to the one end of the light guide 25.

The light guide 25 has the one end connected to the light source device 24 and the other end connected to the imaging unit 21. The light guide 25 transmits the light supplied from the light source device 24 from the one end to the other end to supply the light to the imaging unit 21. The light supplied to the imaging unit 21 is emitted from the imaging unit 21 to the observation target. The light emitted to the observation target and reflected by the observation target (object image) is condensed by the lens unit in the imaging unit 21 and then captured by the image sensor 211.

The control device 26 is provided inside the base unit 22, and collectively controls the operation of the medical observation system 1. As illustrated in FIG. 2, the control device 26 includes a control unit 261 and a storage unit 262.

The control unit 261 is constituted by a central processing unit (CPU), a field-programmable gate array (FPGA), and the like, and collectively controls the operation of the medical observation system 1 in accordance with a control program stored in the storage unit 262.

Specifically, the control unit 261 switches the operation mode of the support unit 23 according to the operation of the operator to a brake release switch 214 (FIGS. 1 and 2) provided on the imaging unit 21.

In the first embodiment, a free mode and a fixed mode are provided as operation modes of the support unit 23.

The free mode is a mode in which the first to sixth state-switching units 234a to 234f are each in the permission state. That is, in the free mode, the operator may rotate the imaging unit 21 about the first to sixth axes O1 to O6 by applying an external force to the support unit 23. The free mode is set while the operator is pressing the brake release switch 214.

The fixed mode is a mode in which the first to sixth state-switching units 234a to 234f are each in the restriction state. That is, in the fixed mode, the operator may not rotate the imaging unit 21 about the first to sixth axes O1 to O6 although applying an external force to the support unit 23. The fixed mode is set while the operator is not pressing the brake release switch 214.

The control unit 261 further performs a registration process for registering the position of the imaging unit 21 and a reproduction process for reproducing the position of the imaging unit 21 at the registered position. The details of the registration process and the reproduction process will be described later.

The control unit 261 further performs various image processes on the captured image obtained by imaging of the imaging unit 21, and generates a video signal for display. Then, the control unit 261 outputs the video signal to the display device 3.

The storage unit 262 stores information and the like necessary for processes of the control unit 261 in addition to the control program executed by the control unit 261.

The display device 3 is constituted by a display using liquid crystal, organic electro luminescence (EL), or the like, and displays the captured image based on the video signal from the control unit 261 (the captured image obtained by imaging of the imaging unit 21).

Registration Process

Next, the registration process performed by the control unit 261 is described.

Figure 3:
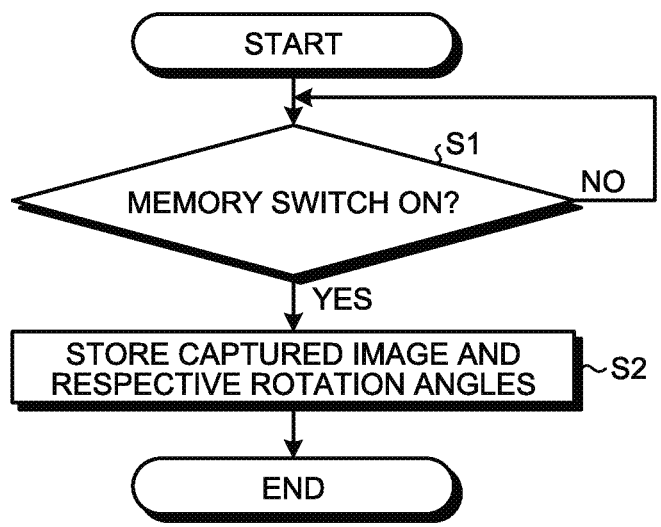
FIG. 3 is a flowchart illustrating a registration process.
Figure 4:
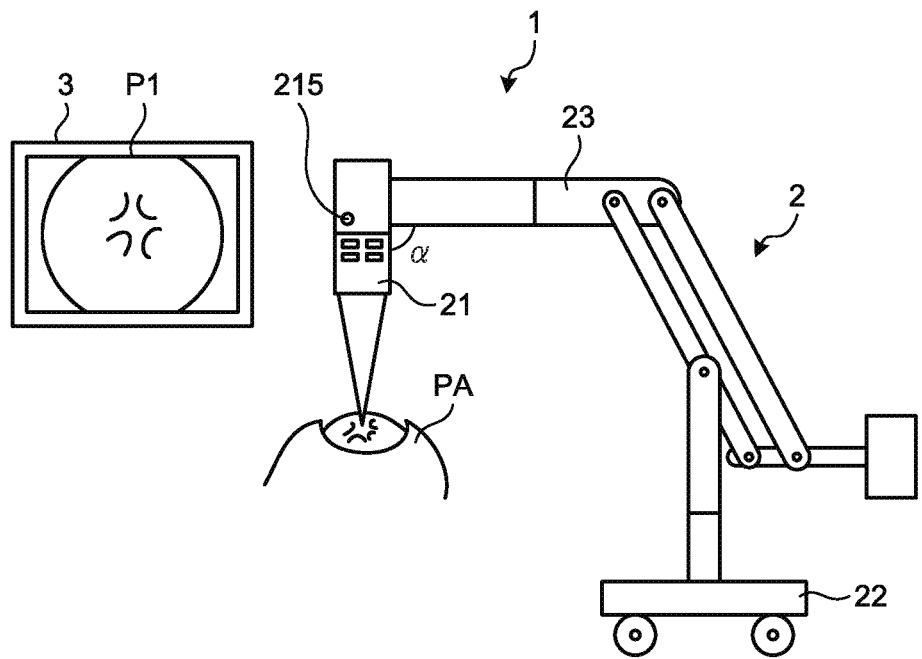
FIG. 4 is a diagram for explaining a registration process and a reproduction process.
Figure 5:
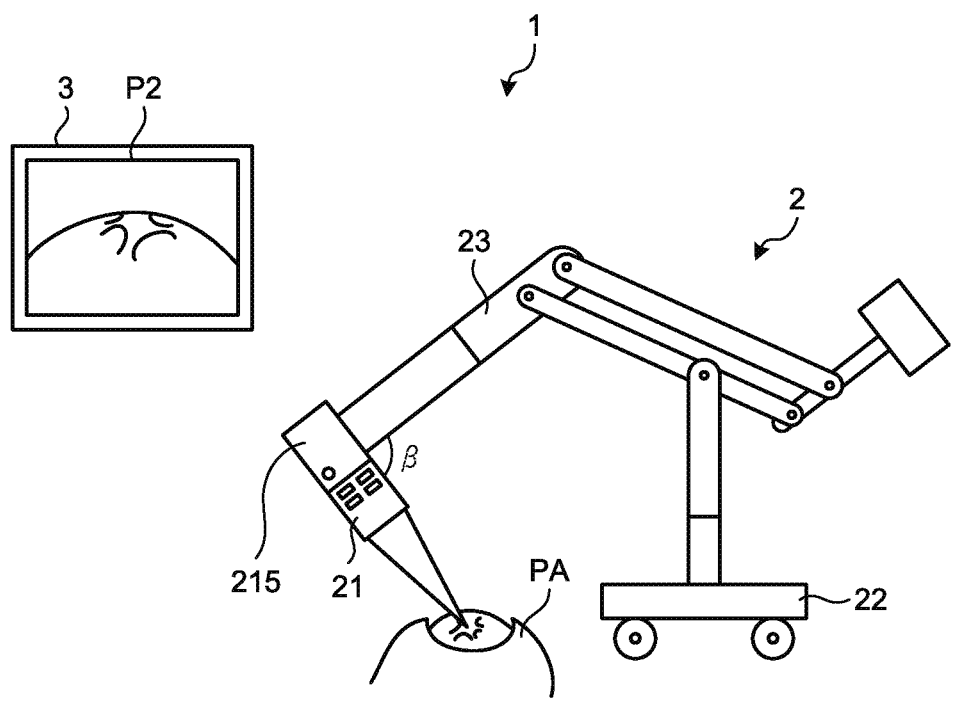
FIG. 5 is a diagram for explaining the registration process and the reproduction process.

FIG. 3 is a flowchart illustrating the registration process. FIGS. 4 and 5 are diagrams for explaining the registration process and the reproduction process.

First, the operator presses the brake release switch 214 while holding the imaging unit 21. The control unit 261 thereby sets the support unit 23 to the free mode. Then, the operator operates the support unit 23 by applying an external force to the support unit 23 via the imaging unit 21 while keeping pressing the brake release switch 214 to locate the imaging unit 21 above the observation target (for example, the head) of a patient PA lying on an operating table (FIG. 4). In the following description, the position of the imaging unit 21 illustrated in FIG. 4 is referred to as a storage position. Then, the operator releases the brake release switch 214. The control unit 261 thereby sets the support unit 23 to the fixed mode.

A captured image P1 obtained by imaging of the imaging unit 21 is displayed on the display device 3 (FIG. 4) supported by a movable stand (not illustrated).

Then, the operator presses a memory switch 215 (FIGS. 1, 2, and 4) provided on the imaging unit 21. By pressing the memory switch 215 (step S1: Yes), the control unit 261 causes the storage unit 262 to store the captured image P1 obtained by imaging of the imaging unit 21 (the captured image to be used in the analysis method described above) and the respective rotation angles detected at the storage position by the first to sixth imaging-position detecting units 235a to 235f (step S2).

After step S2, the operator proceeds with a treatment (surgery) while checking the captured image displayed on the display device 3. At this time, the operator sets the support unit 23 to the free mode by pressing the brake release switch 214 while holding the imaging unit 21, and appropriately changes the posture of the support unit 23 by applying an external force to the support unit 23 via the imaging unit 21 so that the position where the operator wants to perform the treatment is displayed near the center of the screen of the display device 3 (FIG. 5). Then, the operator sets the support unit 23 to the fixed mode by releasing the brake release switch 214 when the support unit 23 is in an appropriate posture.

That is, the position of the imaging unit 21 after the treatment (the posture of the support unit 23 (FIG. 5), hereinafter, referred to as a treatment position) significantly differs from the storage position of the imaging unit 21 before the treatment (the posture of the support unit 23) (FIG. 4).

Reproduction Process

Next, the reproduction process performed by the control unit 261 is described.

Figure 6:
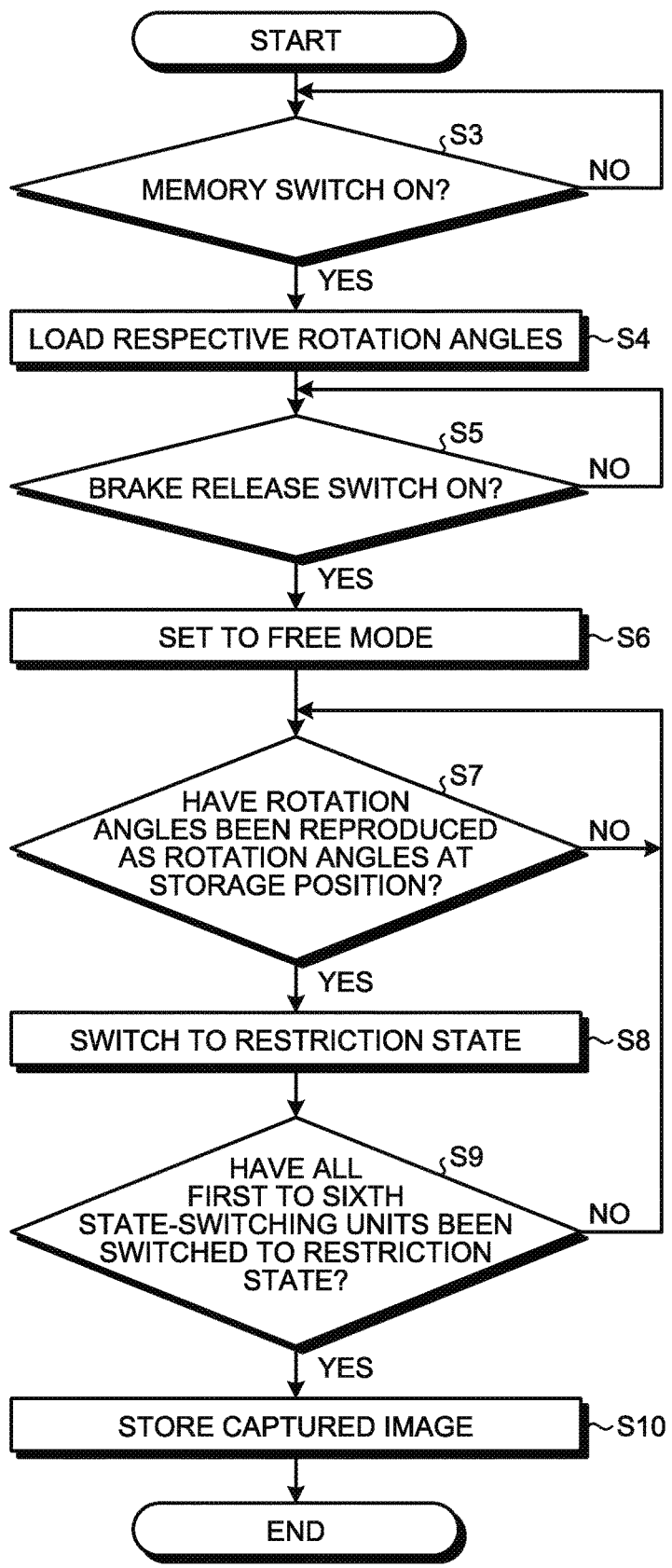
FIG. 6 is a flowchart illustrating a reproduction process.

FIG. 6 is a flowchart illustrating the reproduction process.

First, the operator presses the memory switch 215 in order to return the position of the imaging unit 21 from the treatment position (FIG. 5) to the storage position (FIG. 4). By pressing the memory switch 215 (step S3: Yes), the control unit 261 loads the respective rotation angles stored in the storage unit 262 in step S2 (step S4).

In addition, the operator presses the brake release switch 214 while holding the imaging unit 21. By pressing the brake release switch 214 (step S5: Yes), the control unit 261 sets the support unit 23 to the free mode (step S6). Then, the operator starts moving the imaging unit 21 from the treatment position toward the storage position by applying an external force to the support unit 23 via the imaging unit 21 while keeping pressing the brake release switch 214.

After step S6, the control unit 261 constantly monitors the respective rotation angles currently detected by the first to sixth imaging-position detecting units 235a to 235f, and determines whether the respective rotation angles have been reproduced as the respective rotation angles at the storage position (the respective rotation angles loaded in step S4) (step S7).

For example, it is assumed that the rotation angle detected at the storage position by the second imaging-position detecting unit 235b (the rotation angle stored in the storage unit 262) is an angle α (FIG. 4), and that the rotation angle currently detected by the second imaging-position detecting unit 235b is an angle β (FIG. 5). In this case, when the angle β is the same as the angle α by the operator moving the imaging unit 21 from the treatment position toward the storage position, the rotation angle at the second joint part 232b is reproduced as the rotation angle at the storage position.

When determining that the rotation angle has been reproduced as the rotation angle at the storage position (step S7: Yes), the control unit 261 switches, among the first to sixth joint parts 232a to 232f, the state-switching unit provided in the joint part at which the rotation angle is reproduced to the restriction state (step S8).

After step S8, by determining that the respective rotation angles at all the first to sixth joint parts 232a to 232f have been reproduced as the respective rotation angles at the storage position (step S7: Yes) and performing step S8, the control unit 261 determines whether all the first to sixth state-switching units 234a to 234f have been switched to the restriction state (step S9).

When determining that all the first to sixth state-switching units 234a to 234f have not been switched to the restriction state (step S9: No), the control unit 261 repeatedly performs steps S7 and S8 until all the first to sixth state-switching units 234a to 234f are switched to the restriction state. On the other hand, when determining that all the first to sixth state-switching units 234a to 234f have been switched to the restriction state (step S9: Yes), the control unit 261 causes the storage unit 262 to store the captured image obtained by imaging of the imaging unit 21 (captured image to be used in the analysis method described above) at the time when the storage position has been reproduced (step S10).

Then, the control unit 261 terminates the reproduction process.

According to the first embodiment described above, the following effects are obtained.

In the medical observation apparatus 2 according to first embodiment, the control unit 261 performs the above reproduction process. Thus, when the imaging unit 21 is moved from the treatment position toward the storage position by the operator, the rotation of the first to sixth joint parts 232a to 232f is restricted sequentially from the one at which the rotation angle at the storage position has been reproduced, and the degree of freedom of the support unit 23 is gradually decreased. When all the rotation angles at the first to sixth joint parts 232a to 232f are reproduced as the respective rotation angles at the storage position, all the first to sixth state-switching units 234a to 234f are switched to the restriction state, and the position of the imaging unit 21 is reproduced at the storage position.

Thus, the operator does not need to finely adjust the position of the imaging unit 21 to the storage position in order to reproduce the storage position of the imaging unit 21, and may easily reproduce the storage position of the imaging unit 21 since the degree of freedom of the support unit 23 is gradually decreased by moving around the storage position. In addition, since the support unit 23 is a balance arm, it is possible to perform the operation with a light force. Furthermore, since all the first to sixth joint parts 232a to 232f are not provided with actuators, it is possible to reduce the costs of the medical observation apparatus 2.

As described above, with the medical observation apparatus 2 according to the first embodiment, it is possible to improve convenience while reducing costs.

Second Embodiment

Next, a second embodiment is described.

In the following description, the same components as those in the first embodiment are denoted by the same reference signs, and the detailed description thereof will be omitted or simplified.

Figure 7:
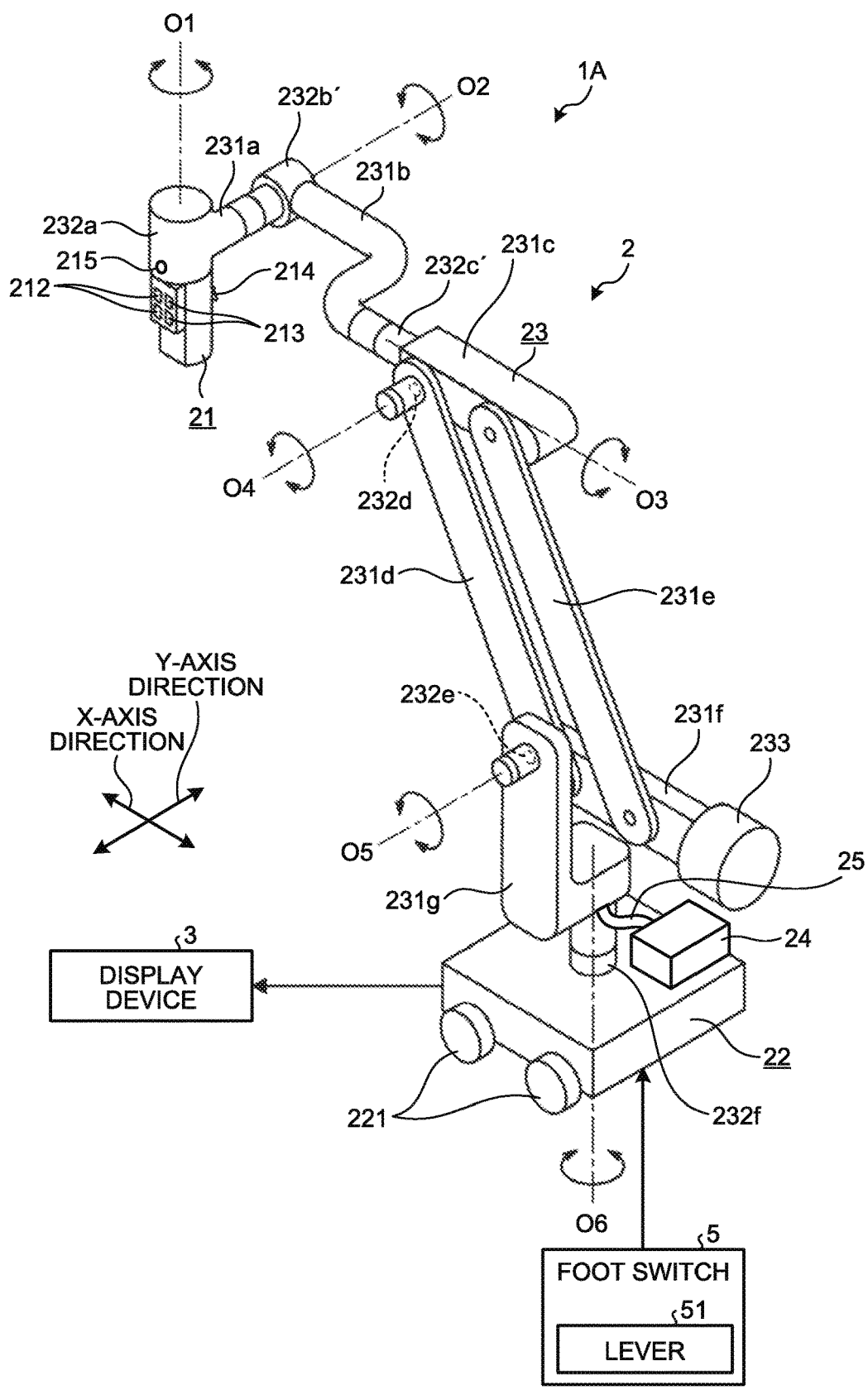
FIG. 7 is a diagram illustrating a medical observation system according to a second embodiment.

FIG. 7 is a diagram illustrating a medical observation system 1A according to the second embodiment.

In first embodiment, the first to sixth axes O1 to O6 have been each constituted by a passive shaft.

In contrast, in the second embodiment, while the first and fourth to sixth axes O1 and O4 to O6 are each constituted by a passive shaft, the second axis O2 is constituted by an active shaft capable of actively rotating the imaging unit 21 about the second axis O2 according to the power of the actuator. Similarly, the third axis O3 is constituted by an active shaft. That is, as illustrated in FIG. 7, in the medical observation system 1A according to the second embodiment, second and third joint parts 232b' and 232c' are used instead of the second and third joint parts 232b and 232c in the medical observation system 1 described in the first embodiment, and are different from the second and third joint parts 232b and 232c.

Here, the first and fourth to sixth state-switching units 234a and 234d to 234f correspond to respective passive-shaft-side state-switching units according to the present disclosure. The second and third state-switching units 234b and 234c correspond to respective active-shaft-side state-switching units according to the present disclosure.

Figure 8:
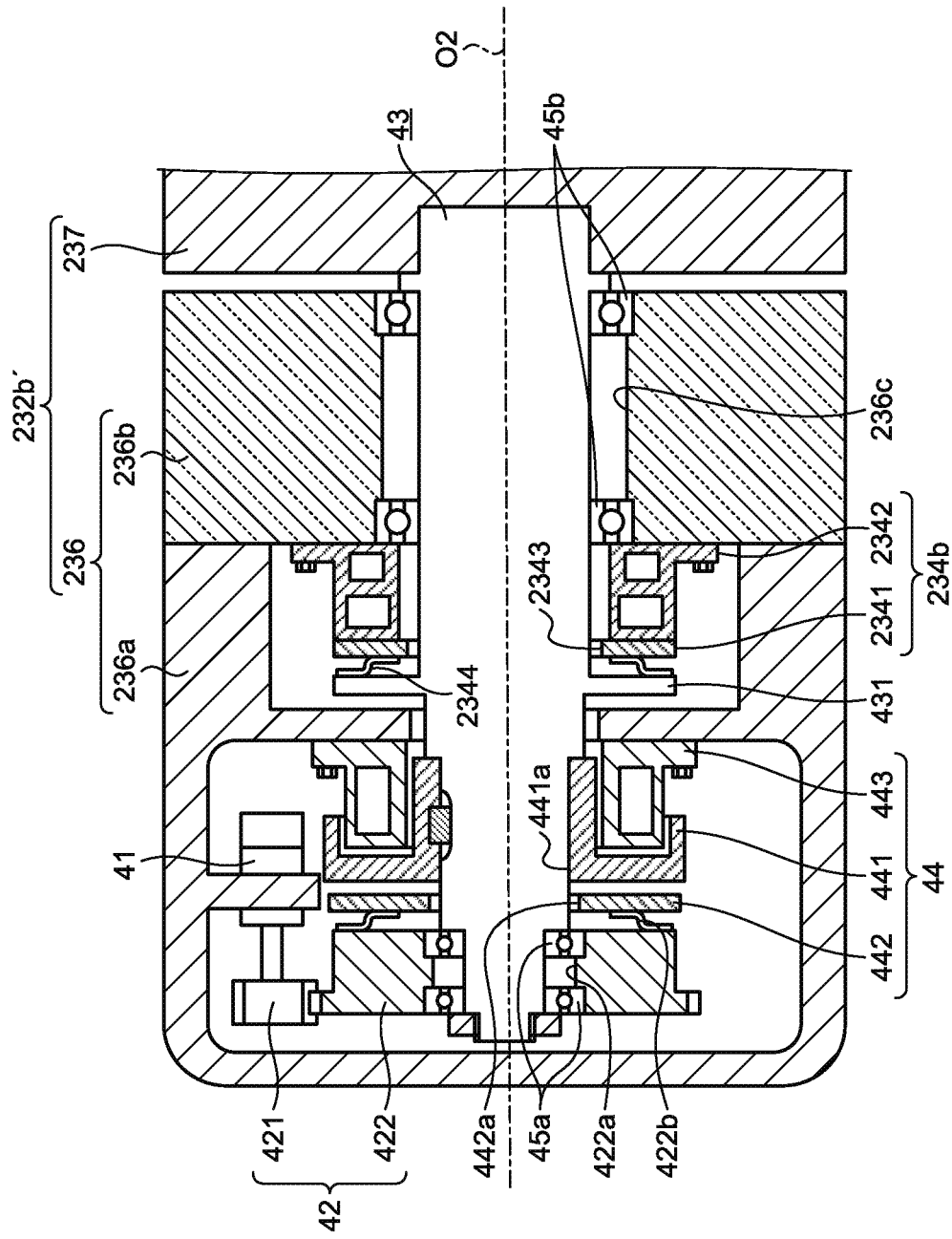
FIG. 8 is a cross-sectional view illustrating a configuration of a second joint part.

FIG. 8 is a cross-sectional view illustrating a configuration of the second joint part 232b'.

The second and third joint parts 232b' and 232c' each have a similar configuration. Thus, the configuration of the second joint part 232b' is described below, and the description of the configuration of the third joint part 232c' is omitted.

As illustrated in FIG. 8, the second joint part 232b' includes a fixed part 236 fixedly supported by the second arm part 231b, and a movable part 237 holding the first arm part 231a and mounted to the fixed part 236 so as to be rotatable about the second axis O2.

The fixed part 236 includes a housing part 236a and a closing part 236b.

The housing part 236a has a bottomed cylindrical shape whose central axis aligns with the second axis O2, and is fixedly supported by the second arm part 231b.

The closing part 236b has an annular shape having a through hole 236c, and is fixed to the housing part 236a so as to close the opening part of the housing part 236a.

In addition, as illustrated in FIG. 8, an actuator 41, a deceleration mechanism 42, a drive shaft 43, a clutch 44, the second state-switching unit 234b, and the second imaging-position detecting unit 235b are provided inside the fixed part 236. In FIG. 8, the illustration of the second imaging-position detecting unit 235b is omitted for convenience of explanation.

The actuator 41 is constituted by a general electric motor controlled by the control unit 261, and is a power source that supplies power to the second joint part 232b'. The actuator 41 is mounted to the inside of the housing part 236a so that the output shaft of the actuator 41 is parallel to the second axis O2.

As illustrated in FIG. 8, the deceleration mechanism 42 is provided on the output shaft of the actuator 41, and decelerates the rotation of the output shaft at a predetermined reduction ratio. The deceleration mechanism 42 includes a plurality of gears that mesh with each other. In the second embodiment, the plurality of gears includes a first spur gear 421 fixed to the output shaft of the actuator 41, and a second spur gear 422 meshing with the first spur gear 421.

Note that, the number of gears constituting the deceleration mechanism 42 is not limited to two as described above, and may be three or more. In addition, the gears constituting the deceleration mechanism 42 are not limited to spur gears, and may be other gears.

The second spur gear 422 of the first and second spur gears 421 and 422 is disposed inside the housing part 236a so that the central axis thereof aligns with the second axis O2. In addition, the second spur gear 422 is formed with a through hole 422a passing therethrough along the central axis.

As illustrated in FIG. 8, the drive shaft 43 has a cylindrical shape, and is installed so that the central axis of the cylinder aligns with the second axis O2. Specifically, one end of the drive shaft 43 is inserted in the through hole 422a, and is pivotally supported so as to be rotatable with respect to the second spur gear 422 via a first bearing 45a. Furthermore, the other end of the drive shaft 43 is inserted in the through hole 236c, and is pivotally supported so as to be rotatable with respect to the closing part 236b via a second bearing 45b while the other end is projecting to the outside of the fixed part 236. That is, the drive shaft 43 is rotatable about the central axis with respect to the fixed part 236. The other end of the drive shaft 43 is fixed to the movable part 237.

As illustrated in FIG. 8, the clutch 44 includes a rotor 441, an armature 442, and a stator 443.

The rotor 441 includes a through hole 441a, and is fixed to the drive shaft 43 while the drive shaft 43 is being inserted in the through hole 441a.

The armature 442 has a disc shape and includes a through hole 442a passing therethrough along the central axis of the disc. The armature 442 is disposed between the second spur gear 422 and the rotor 441 while the drive shaft 43 is being inserted in the through hole 442a. The armature 442 is attached to the second spur gear 422 via a leaf spring 442b and is movable along the second axis O2 according to the elastic deformation of the leaf spring 442b.

The stator 443 is fixed to the housing part 236a, and moves the armature 442 forward and backward along the second axis O2 under the control of the control unit 261. While the armature 442 is being separated from the rotor 441, the deceleration mechanism 42 and the drive shaft 43 are in a disconnected state in which they are not connected via the clutch 44 (clutch OFF). That is, the drive shaft 43 does not rotate according to the rotation of the actuator 41. On the other hand, while the armature 442 is in contact with the rotor 441, the deceleration mechanism 42 and the drive shaft 43 are in a connected state in which they are connected via the clutch 44 (clutch ON). That is, the drive shaft 43 rotates according to the rotation of the actuator 41, transmits the rotation of the actuator 41 to the movable part 237, and rotates the movable part 237 (imaging unit 21) about the second axis O2.

The second state-switching unit 234b includes an armature 2341 and a stator 2342 as illustrated in FIG. 8.

The armature 2341 has a disc shape and includes a through hole 2343 passing therethrough along the central axis of the disc, and the drive shaft 43 is inserted in the through hole 2343. The armature 2341 is attached to a flange 431 provided on the outer peripheral surface of the drive shaft 43 via a leaf spring 2344, and is movable along the second axis O2 according to the elastic deformation of the leaf spring 2344.

The stator 2342 is fixed to the closing part 236b, and moves the armature 2341 forward and backward along the second axis O2 under the control of the control unit 261. While the armature 2341 is being separated from the stator 2342, the stator 2342 releases the armature 2341 and permits the drive shaft 43 to rotate. That is, the second state-switching unit 234b is in the permission state. On the other hand, while the armature 2341 is in contact with the stator 2342, the stator 2342 restricts the rotation of the armature 2341 (drive shaft 43). That is, the second state-switching unit 234b is in the restriction state.

In the second embodiment, as the operation modes of the support unit 23, an XY movement operation mode is provided in addition to the free mode and the fixed mode described in the first embodiment.

The XY movement operation mode is an operation mode in which the imaging field of the imaging unit 21 is moved in the X-axis direction and the Y-axis direction according to an operation of the operator to a foot switch 5 (FIG. 7).

More specifically, while the operator is operating a lever 51 (FIG. 7) of the foot switch 5 in the X direction, the control unit 261 switches the second state-switching unit 234b and the clutch 44 to the permission state and the connected state (clutch ON) respectively, and operates the actuator 41. The imaging unit 21 is thereby rotated about the second axis O2. In addition, when the operator stops operating the lever 51 in the X direction, the control unit 261 stops operating the actuator 41, and switches the clutch 44 and the second state-switching unit 234b to the disconnected state (clutch OFF) and the restriction state respectively.

Alternatively, while the operator is operating the lever 51 of the foot switch 5 in the Y direction, the control unit 261 switches the third state-switching unit 234c and the clutch provided (not illustrated) in the third joint part 232c' to the permission state and the connected state (clutch ON) respectively, and operates the actuator provided in the third joint part 232c'. The imaging unit 21 is thereby rotated about the third axis O3. In addition, when the operator stops operating the lever 51 in the Y direction, the control unit 261 stops operating the actuator, and switches the clutch and the third state-switching unit 234c to the disconnected state (clutch OFF) and the restriction state respectively.

Next, a reproduction process according to the second embodiment is described. Note that, a registration process according to the second embodiment is similar to the registration process described in the first embodiment.

Figure 9:
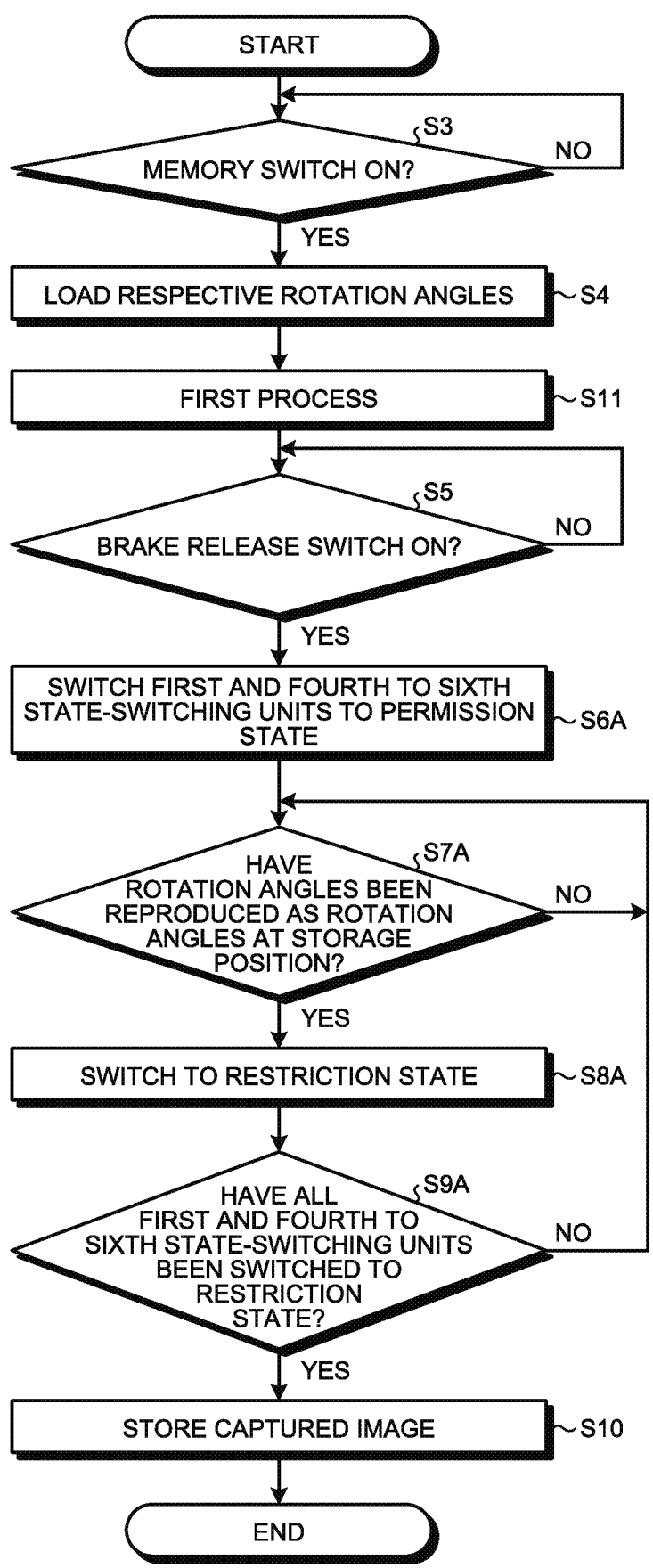
FIG. 9 is a flowchart illustrating a reproduction process.

FIG. 9 is a flowchart illustrating the reproduction process.

In the reproduction process according to the second embodiment, as illustrated in FIG. 9, step S11 is added to the reproduction process described in the first embodiment, and steps S6A to S9A are performed instead of steps S6 to S9. Thus, steps S11 and S6A to S9A are described below.

Note that, in the second embodiment, as the operation modes of the support unit 23, the XY movement operation mode is provided in addition to the free mode and the fixed mode described in the first embodiment. Thus, the operator may locate the imaging unit 21 at the storage position or the treatment position using at least one of the free mode and the XY movement operation mode.

Step S11 is performed after step S4.

Specifically, in step S11, the control unit 261 performs a first process as described below.

The control unit 261 switches the second state-switching unit 234b and the clutch 44 to the permission state and the connected state (clutch ON) respectively. Then, the control unit 261 operates the actuator 41 until the rotation angle currently detected by the second imaging-position detecting unit 235b is the same as the rotation angle detected at the storage position by the second imaging-position detecting unit 235b (the rotation angle loaded in step S4). Then, the control unit 261 stops operating the actuator 41, and switches the clutch 44 and the second state-switching unit 234b to the disconnected state (clutch OFF) and the restriction state respectively.

In addition, the control unit 261 switches the third state-switching unit 234c and the clutch provided in the third joint part 232c' to the permission state and the connected state (clutch ON) respectively. Then, the control unit 261 operates the actuator provided in the third joint part 232c' until the rotation angle currently detected by the third imaging-position detecting unit 235c is the same as the rotation angle detected at the storage position by the third imaging-position detecting unit 235c (the rotation angle loaded in step S4). Then, the control unit 261 stops operating the actuator, and switches the clutch and the third state-switching unit 234c to the disconnected state (clutch OFF) and the restriction state respectively.

That is, with the first process (step S11), the rotation angle at the second joint part 232b' and the rotation angle at the third joint part 232c' are automatically reproduced as the respective rotation angles at the storage position.

After step S11, the operator presses the brake release switch 214 while holding the imaging unit 21. By pressing the brake release switch 214 (step S5: Yes), the control unit 261 switches, among the first to sixth state-switching units 234a to 234f, the first and fourth to sixth state-switching units 234a and 234d to 234f to the permission state (step S6A). Then, the operator starts moving the imaging unit 21 toward the storage position by applying an external force to the support unit 23 via the imaging unit 21 while keeping pressing the brake release switch 214.

After step S6A, the control unit 261 constantly monitors the respective rotation angles currently detected by the first and fourth to sixth imaging-position detecting units 235a and 235d to 235f, and determines whether the respective rotation angles have been reproduced as the respective rotation angles at the storage position (the respective rotation angles loaded in step S4) (step S7A).

When determining that the respective rotation angles have been reproduced as the respective rotation angles at the storage position (step S7A: Yes), the control unit 261 switches, among the first and fourth to sixth joint parts 232a and 232d to 232f, the state-switching units provided in the joint parts at which the rotation angles have been reproduced to the restriction state (step S8A).

After step S8A, by determining that the respective rotation angles of all the first and fourth to sixth joint parts 232a and 232d to 232f have been reproduced as the respective rotation angles at the storage position (step S7A: Yes) and performing step S8A, the control unit 261 determines whether all the first and fourth to sixth state-switching units 234a and 234d to 234f have been switched to the restriction state (step S9A).

When determining that all the first and fourth to sixth state-switching units 234a and 234d to 234f have not been switched to the restriction state (step S9A: No), the control unit 261 repeatedly performs steps S7A and S8A until all the first and fourth to sixth state-switching units 234a and 234d to 234f are switched to the restriction state. On the other hand, when determining that all the first and fourth to sixth state-switching units 234a and 234d to 234f have been switched to the restriction state (step S9A: Yes), the control unit 261 proceeds to step S10.

Steps S6A to S9A described above correspond to a second process according to the present disclosure.

According to the second embodiment described above, the following effects are obtained in addition to similar effects to those in the first embodiment.

In second embodiment, the control unit 261 performs the first and second processes. That is, with the first process, the rotation angle at the second joint part 232b' and the rotation angle at the third joint part 232c' are automatically reproduced as the respective rotation angles at the storage position. Thus, in order to reproduce the storage position of the imaging unit 21, the operator is only required to reproduce the rotation angles only at the first and fourth to sixth joint parts 232a and 232d to 232f as the respective rotation angles at the storage position. Accordingly, the degree of freedom for the operator to operate is reduced, and it is possible to further improve convenience.

Third Embodiment

Next, a third embodiment is described.

In the following description, the same components as those in the first embodiment are denoted by the same reference signs, and the detailed description thereof will be omitted or simplified.

Figure 10:
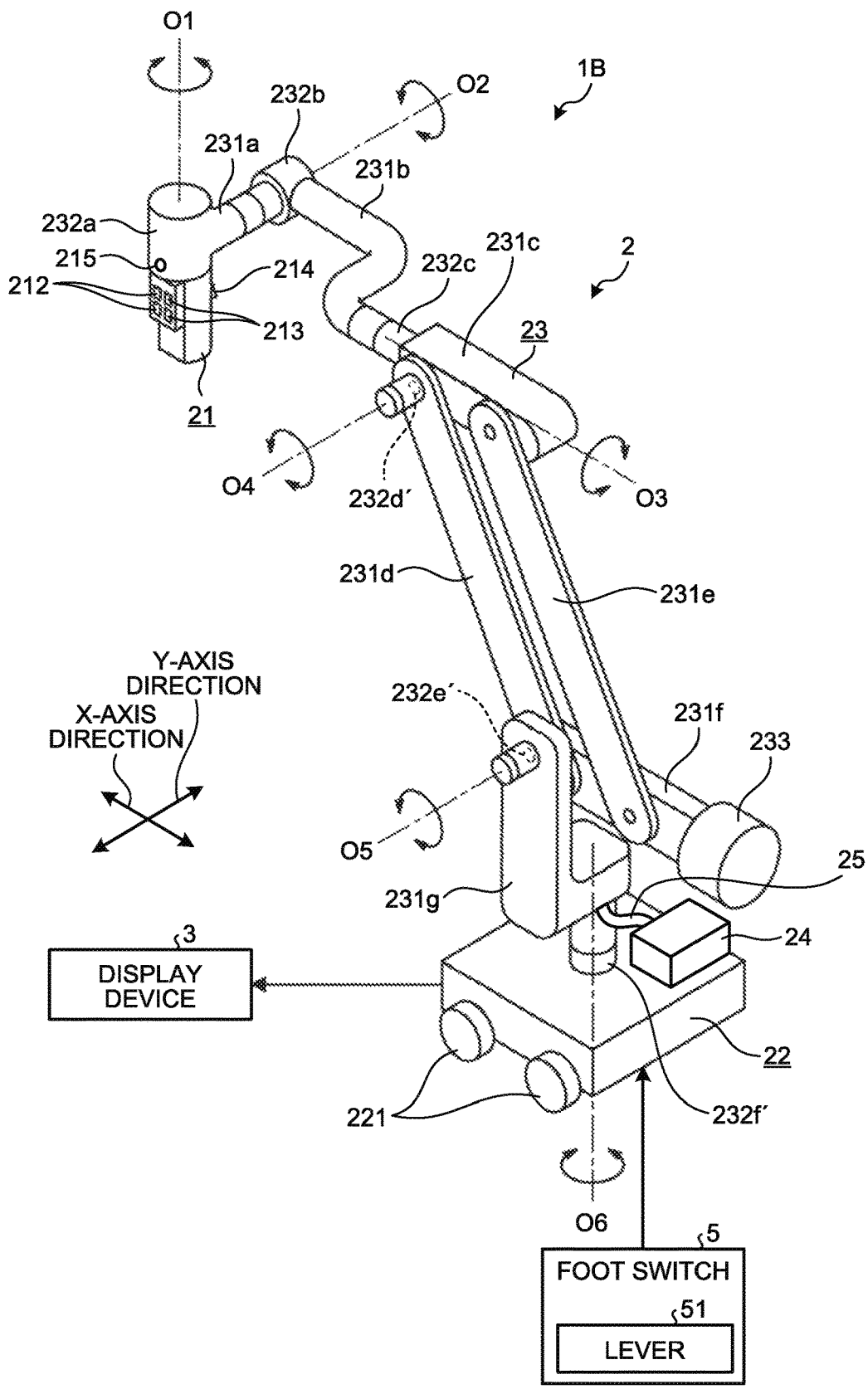
FIG. 10 is a diagram illustrating a medical observation system according to a third embodiment.

FIG. 10 is a diagram illustrating a medical observation system 1B according to the third embodiment.

In first embodiment, the first to sixth axes O1 to O6 have been each constituted by a passive shaft.

In contrast, in the third embodiment, while the first to third axes O1 to O3 are each constituted by a passive shaft, the fourth to sixth axes O4 to O6 are each constituted by an active shaft. That is, in the medical observation system 1B according to the third embodiment, as illustrated in FIG. 10, fourth to sixth joint parts 232d', 232e', and 232f' are used instead of the fourth to sixth joint parts 232d to 232f in the medical observation system 1 described in the first embodiment, and are different from the fourth to sixth joint parts 232d to 232f.

Here, the fourth to sixth state-switching units 234d to 234f correspond to respective active-shaft-side state-switching units according to the present disclosure. The first to third state-switching units 234a to 234c correspond to passive-shaft-side state-switching units according to the present disclosure.

The fourth to sixth joint parts 232d', 232e', and 232f' each have a similar configuration to the second joint part 232b' described in the second embodiment.

In a reproduction process according to the third embodiment, the respective rotation angles at the fourth to sixth joint parts 232d', 232e', and 232f' are automatically reproduced as the respective rotation angles at the storage position with the first process (step S11), and the respective rotation angles at the first to third joint parts 232a to 232c are reproduced as the respective rotation angles at the storage position with the second process (steps S6A to S9A) using the operation of the operator, similarly to the reproduction process described in the second embodiment.

According to the third embodiment described above, similar effects to those in the second embodiment are obtained.

Fourth Embodiment

Next, a fourth embodiment is described.

In the following description, the same components as those in the first embodiment are denoted by the same reference signs, and the detailed description thereof will be omitted or simplified.

Figure 11:
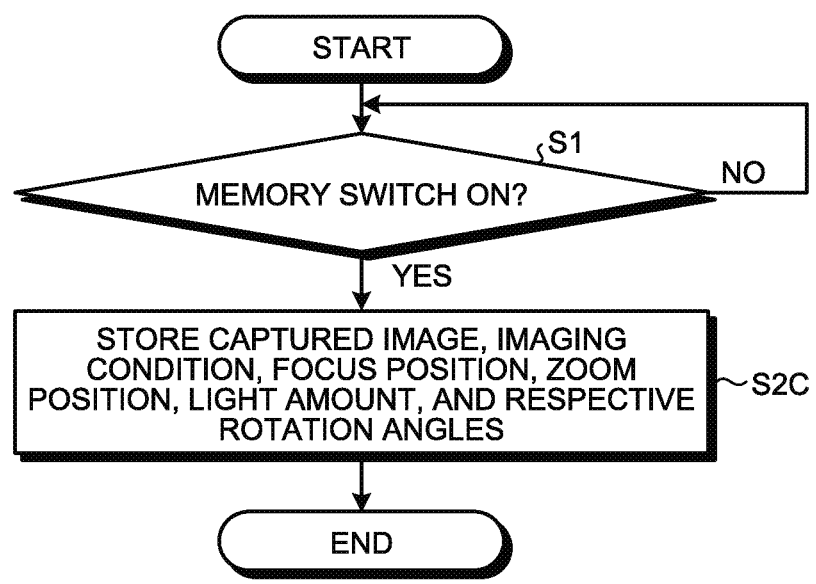
FIG. 11 is a flowchart illustrating a registration process according to a fourth embodiment.
Figure 12:
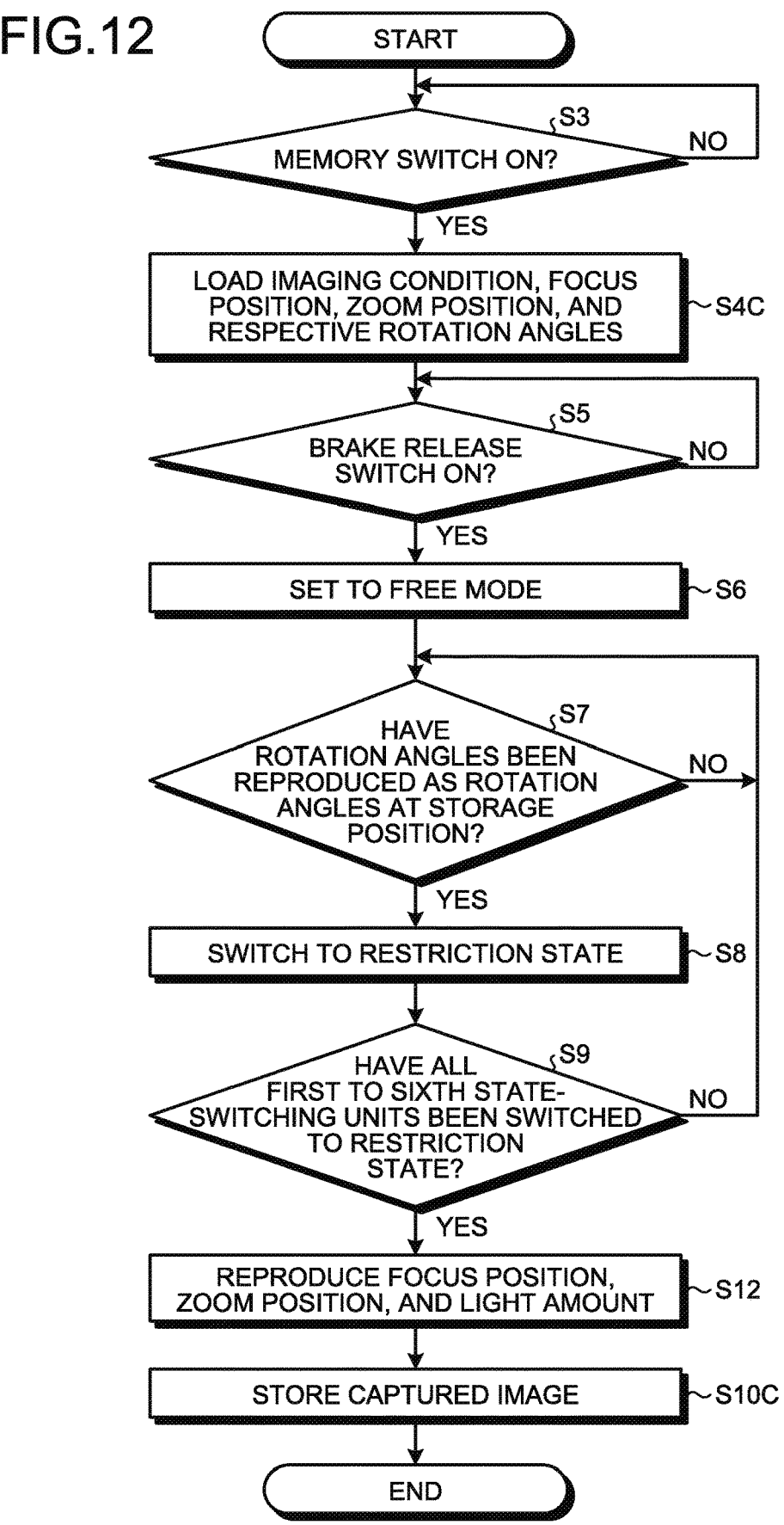
FIG. 12 is a flowchart illustrating a reproduction process according to the fourth embodiment.

FIG. 11 is a flowchart illustrating a registration process according to the fourth embodiment. FIG. 12 is a flowchart illustrating a reproduction process according to the fourth embodiment.

In the fourth embodiment, as illustrated in FIGS. 11 and 12, the registration process and the reproduction process performed by the control unit 261 are different from those in the first embodiment.

Before the registration process and the reproduction process are described, an imaging unit 21C according to the fourth embodiment is described.

Figure 13:
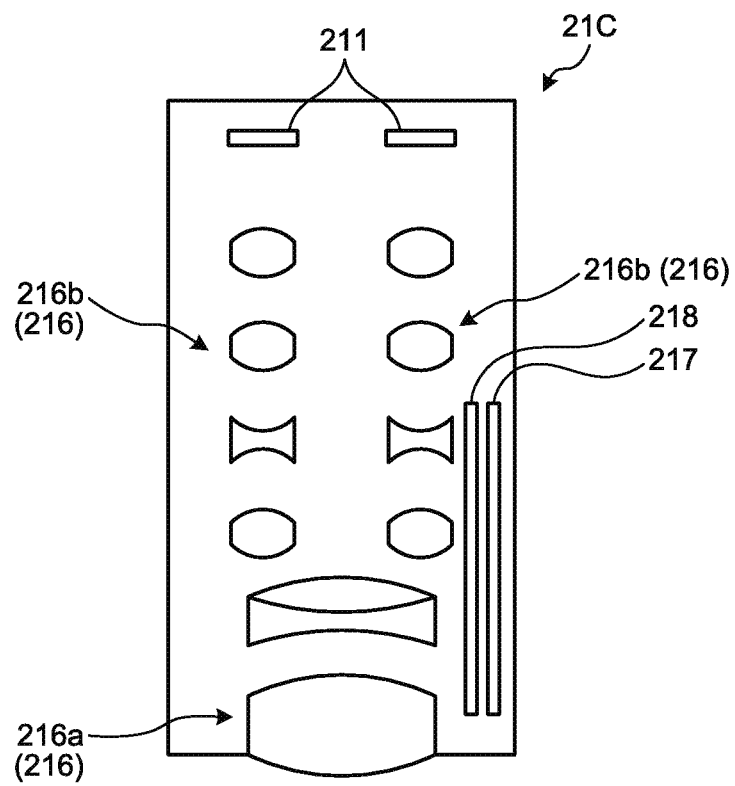
FIG. 13 is a diagram illustrating a configuration of an imaging unit.

FIG. 13 is a diagram illustrating the imaging unit 21C according to the fourth embodiment. In FIG. 13, the illustration of the switches 212 to 215 provided to be exposed on the outer surface of the imaging unit 21C is omitted for convenience of explanation. FIG. 13 illustrates, as an example, that the imaging unit 21C is configured as what is called a stereo camera.

In the fourth embodiment, the imaging unit 21C (FIG. 13) is used instead of the imaging unit 21.

As illustrated in FIG. 13, the imaging unit 21C includes an image sensor 211, a lens unit 216, a driving unit 217, and a lens-position detecting unit 218.

The lens unit 216 includes a focus optical system 216a and a zoom optical system 216b, captures an object image of an observation target, and forms the image on the imaging surface of the image sensor 211.

The focus optical system 216a is constituted by one or a plurality of lenses, and adjusts the focus by moving along the optical axis. That is, the focus optical system 216a corresponds to a focus lens according to the present disclosure.

The zoom optical system 216b is constituted by one or a plurality of lenses, and adjusts the field angle by moving along the optical axis. That is, the zoom optical system 216b corresponds to a zoom lens according to the present disclosure.

The lens unit 216 is provided with a focus mechanism (not illustrated) for moving the focus optical system 216a along the optical axis, and an optical zoom mechanism (not illustrated) for moving the zoom optical system 216b along the optical axis.

The driving unit 217 operates the focus mechanism and the optical zoom mechanism under the control of the control unit 261 to adjust the focus and the field angle of the lens unit 216. That is, the driving unit 217 corresponds to a focus driving unit and a zoom driving unit according to the present disclosure.

The lens-position detecting unit 218 is constituted by a position sensor, such as a photo interrupter, and detects the lens position of the focus optical system 216a (hereinafter, referred to as a focus position) and the lens position of the zoom optical system 216b (hereinafter, referred to as a zoom position). That is, the lens-position detecting unit 218 corresponds to a focus-position detecting unit and a zoom-position detecting unit according to the present disclosure. The lens-position detecting unit 218 outputs a signal corresponding to the detected focus position and zoom position to the control device 26.

Next, the registration process according to fourth embodiment is described with reference to FIG. 11.

As illustrated in FIG. 11, in the registration process according to the fourth embodiment, step S2C is performed instead of step S2 in the registration process described in the first embodiment. Thus, step S2C is described below.

In step S2C, the control unit 261 causes the storage unit 262 to store a captured image P1 obtained by imaging of the imaging unit 21C at a storage position, the imaging conditions (the shutter speed, sensitivity, gain, and the like) designated for the imaging unit 21C in the imaging at the storage position, the focus position and zoom position detected by the lens-position detecting unit 218 at the storage position, the light amount designated for the light source device 24 in the imaging at the storage position, and the respective rotation angles detected at the storage position by the first to sixth imaging-position detecting units 235a to 235f.

Next, the reproduction process according to fourth embodiment is described with reference to FIG. 12.

As illustrated in FIG. 12, in the reproduction process according to the fourth embodiment, steps S4C and S10C are performed instead of steps S4 and S10 in the reproduction process described in the first embodiment, and step S12 is further added. Thus, steps S4C, S10C, and S12 are described below.

In step S4C, the control unit 261 loads the imaging conditions, the focus position, the zoom position, and the respective rotation angles stored in the storage unit 262 in step S2C.

Step S12 is performed when the control unit 261 determines that all the first to sixth state-switching units 234a to 234f have been switched to the restriction state (step S9: Yes).

Specifically, the control unit 261 performs the following process in step S12.

The control unit 261 operates the driving unit 217 while constantly monitoring the focus position and zoom position currently detected by the lens-position detecting unit 218, and locates the focus position and zoom position to the focus position and zoom position loaded in step S4C. The control unit 261 further sets the light amount to be designated for the light source device 24 to the light amount loaded in step S4C.

In step S10C, the control unit 261 causes the imaging unit 21 to perform imaging under the imaging conditions loaded in step S4C, and causes the storage unit 262 to store the captured image obtained by the imaging.

According to the fourth embodiment described above, the following effects are obtained in addition to similar effects to those in the first embodiment.

In the fourth embodiment, the control unit 261 performs steps S2C, S4C, S12, and S10C described above. Thus, it is possible to reproduce the imaging conditions, the focus position, the zoom position, and the light amount as the imaging conditions, the focus position, the zoom position, and the light amount at the storage position. Accordingly, in the analysis method described above, it is possible to accurately grasp the condition of the operative site after a treatment.

Fifth Embodiment

Next, a fifth embodiment is described.

In the following description, the same components as those in the first embodiment are denoted by the same reference signs, and the detailed description thereof will be omitted or simplified.

Figure 14:
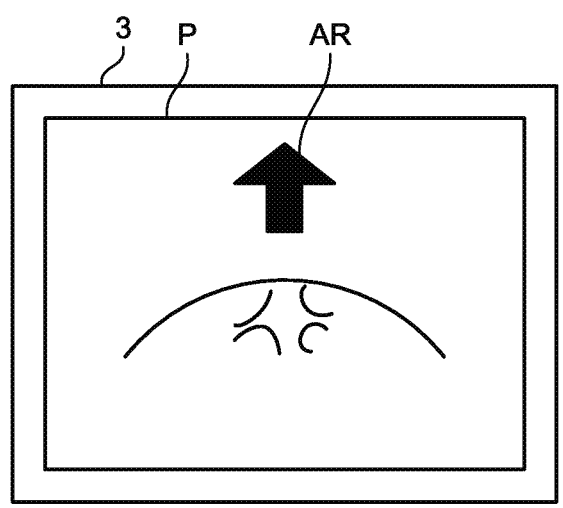
FIG. 14 is a diagram for explaining a reproduction process according to a fifth embodiment.

FIG. 14 is a diagram for explaining a reproduction process according to the fifth embodiment.

In the fifth embodiment, when moving the imaging unit 21 toward the storage position after step S4 in performing the reproduction process described in the first embodiment, the control unit 261 superimposes information AR (FIG. 14) on a captured image P (FIG. 14) and displays it on the display device 3.

Specifically, the control unit 261 calculates the movement direction for moving the imaging unit 21 toward the storage position, based on the respective rotation angles at the storage position loaded in step S4 and the respective rotation angles currently detected by the first to sixth imaging-position detecting units 235a to 235f. Then, the control unit 261 superimposes the movement information AR indicating the movement direction on the captured image P and displays it on the display device 3.

According to the fifth embodiment described above, the following effects are obtained in addition to similar effects to those in the first embodiment.

In the fifth embodiment, the control unit 261 displays the movement information AR on the display device 3. Thus, the operator may recognize, from the movement information AR, the movement direction of the imaging unit 21, and it is possible to easily reproduce the position of the imaging unit 21 at the storage position.

Sixth Embodiment

Next, a sixth embodiment is described.

In the following description, the same components as those in the first embodiment are denoted by the same reference signs, and the detailed description thereof will be omitted or simplified.

Figure 15:
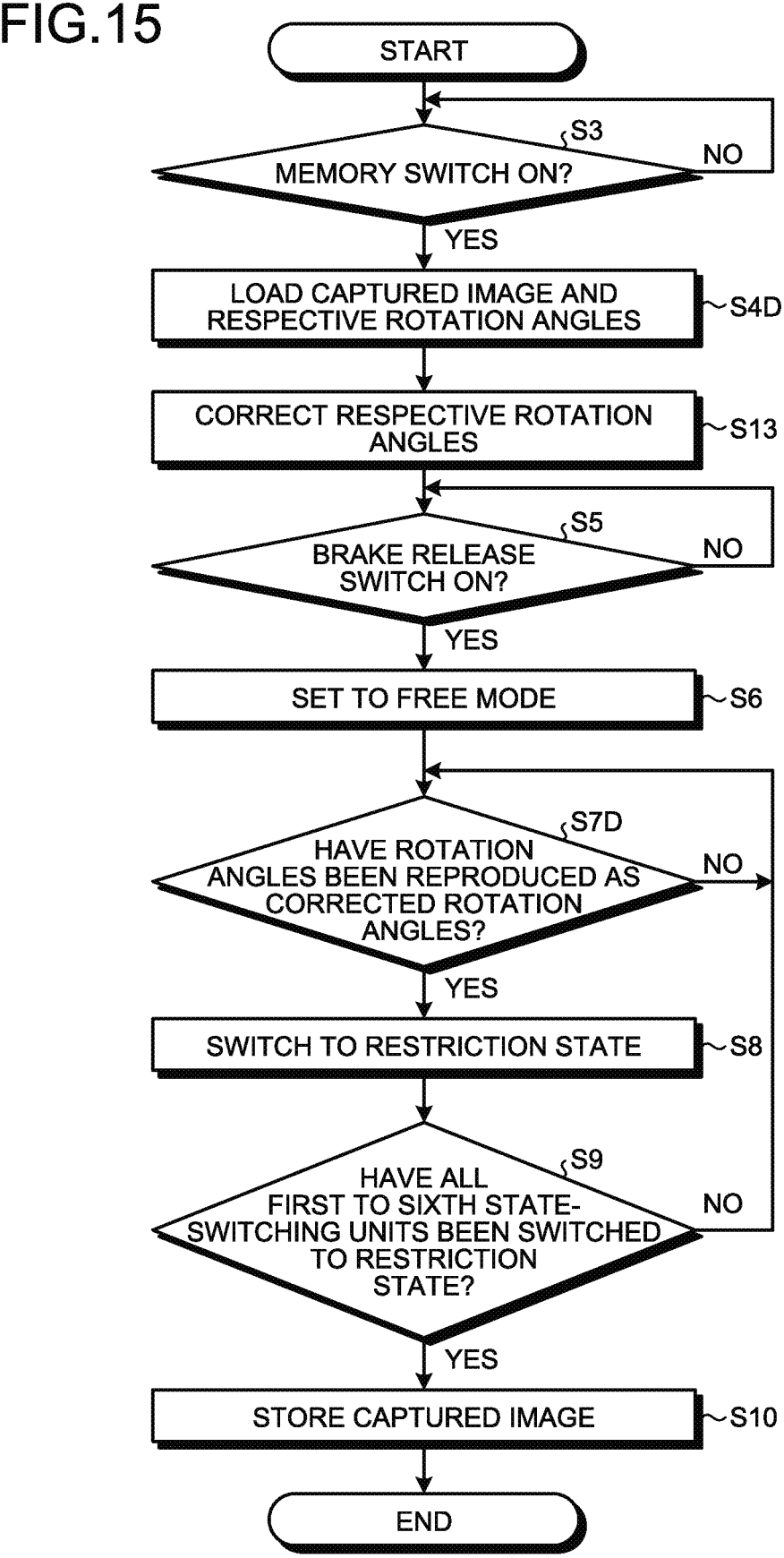
FIG. 15 is a flowchart illustrating a reproduction process according to a sixth embodiment.

FIG. 15 is a flowchart illustrating a reproduction process according to the sixth embodiment.

In the sixth embodiment, as illustrated in FIG. 15, the reproduction process performed by the control unit 261 is different from that in the first embodiment.

Specifically, in the reproduction process according to the sixth embodiment, as illustrated in FIG. 15, step S13 is added to the reproduction process described in the first embodiment, and steps S4D and S7D are performed instead of steps S4 and S7. Thus, steps S13, S4D, and S7D are described below.

In step S4D, the control unit 261 loads the captured image P1 and the respective rotation angles stored in the storage unit 262 in step S2.

After step S4D, the control unit 261 performs the following process (step S13).

The control unit 261 corrects the respective rotation angles loaded in step S4D in consideration of the movement of the observation target based on the captured image P1 loaded in step S4D and a captured image obtained by imaging of the imaging unit 21 at a treatment position (for example, a captured image P2 illustrated in FIG. 5).

In step S7D, the control unit 261 constantly monitors the respective rotation angles currently detected by the first to sixth imaging-position detecting units 235a to 235f, and determines whether the respective rotation angles have been reproduced as (equal to) the respective rotation angles corrected in step S13.

When determining that the respective rotation angles have been reproduced as (equal to) the respective rotation angles corrected in step S13 (step S7D: Yes), the control unit 261 proceeds to step S8.

According to the sixth embodiment described above, the following effect is obtained in addition to similar effects to those in the first embodiment.

In the sixth embodiment, the control unit 261 performs steps S4D, S13, and S7D described above. Thus, although the observation target has moved during the period from the imaging at the storage position to the end of the treatment, it is possible to obtain an appropriate captured image for performing the above analysis method in step S10.

Other Embodiments

The embodiments for carrying out the present disclosure have been described, but the present disclosure should not be limited only by the above first to sixth embodiments.

In the first to sixth embodiments described above, the first to sixth state-switching units 234a to 234f have been provided in the first to sixth joint parts 232a to 232f (232b', 232c', 232d', 232e', 232f) respectively. However, the present disclosure is not limited thereto. A part of the first to sixth state-switching units 234a to 234f (for example, the first state-switching unit 234a) may be omitted.

In fourth embodiment described above, the imaging conditions, the focus position, the zoom position, and the light amount have been reproduced as the imaging conditions, the focus position, the zoom position, and the light amount at the storage position. However, the present disclosure is not limited thereto. At least any one of an imaging condition, a focus position, a zoom position, and a light amount may be reproduced.

In fifth embodiment described above, the movement information indicating the movement direction for moving the imaging unit 21 toward the storage position has been displayed on the display device 3. However, the present disclosure is not limited thereto, and the movement information may be output by sound.

In the first to sixth embodiments described above, a head mounted display may be used as the display device 3.

With a medical observation apparatus and a medical observation system according to the present disclosure, it is possible to improve convenience while reducing costs.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical observation apparatus comprising:
a camera configured to capture an object image of an observation target;
a support configured to support the camera so as to be rotatable about a plurality of mutually-different shafts;
a memory configured to store a storage position of the camera;
a brake configured to switch between: a permission state for permitting the camera to rotate about at least one of the plurality of shafts; and a restriction state for restricting the rotation; and
control circuitry configured to perform a reproduction process for switching the brake to the permission state, and thereafter switching the brake from the permission state to the restriction state when the support is operated according to an external force applied to the support by an operator and the camera is located at the storage position of the camera stored in the memory.

2. The medical observation apparatus according to claim 1, further comprising a position detector configured to detect a position of the camera, wherein
the memory is configured to store the position of the camera detected b the position detector.

3. The medical observation apparatus according to claim 1, wherein each of the plurality of shafts includes a passive shaft configured to passively rotate the camera about the shaft according to the external force applied to the support by the operator.

4. The medical observation apparatus according to claim wherein
the plurality of shafts includes:
a passive shaft configured to passively rotate the camera about the shaft according to the external force applied to the support by the operator; and an active shaft configured to actively rotate the camera about the shaft with a power of an actuator, the brake includes:
a passive-shaft-side brake configured to switch between: the permission state for permitting the camera to rotate about the passive shaft; and the restriction state for restricting the rotation; and
an active-shaft-side brake configured to switch between: the permission state for permitting the camera to rotate about the active shaft; and the restriction state for restricting the rotation, and
the control circuitry is configured to:
switch the active-shaft-side brake to the permission state, and thereafter switch the active-shaft-side brake from the permission state to the restriction state when the actuator is operated and the camera is located at the position of the camera stored in the memory; and
switch the passive-shaft-side brake to the permission state, and thereafter switch the passive-shaft-side brake from the permission state to the restriction state when the support is operated according to the external force applied to the support by the operator and the camera is located at the position of the camera stored in the memory.

5. The medical observation apparatus according to claim 4, wherein the active shaft is a shaft for moving the camera so as to change a direction of an optical axis of the camera with respect to the observation target according to the rotation of the camera about the active shaft.

6. The medical observation apparatus according to claim 4, wherein the active shaft is a shaft for moving the camera in parallel according to the rotation of the camera about the active shaft.

7. The medical observation apparatus according to claim 1, wherein
the camera includes:
an image sensor configured to capture the object image;
a lens unit including a focus lens whose focal point is adjusted by moving along an optical axis, the lens unit being configured to form the object image on the image sensor;
a focus driver configured to move the focus lens along the optical axis; and
a focus-position detector configured to detect a position of the focus lens,
the memory is configured to store the position of the focus lens detected by the focus-position detector, and
the control circuitry, in performing the reproduction process, is configured to control the focus driver and move the focus lens to the position of the focus lens stored in the memory.

8. The medical observation apparatus according to claim 1, wherein
the camera includes:
an image sensor configured to capture the object image;
a lens unit including a zoom lens whose field angle is adjusted by moving along an optical axis, the lens unit being configured to form the object image on the image sensor;
a zoom driver configured to move the zoom lens along the optical axis; and
a zoom-position detector configured to detect a. position of the zoom lens,
the memory is configured to store the position of the zoom lens detected by the zoom-position detector, and the control circuitry, in performing the reproduction process, configured to control the zoom driver and move the zoom lens to the position of the zoom lens stored in the memory.

9. The medical observation apparatus according to claim 1, further comprising a light source configured to emit illumination light for irradiating the observation target with a light amount designated by the control circuitry, wherein
the memory is configured to store the light amount of the illumination light from the light source, and
the control circuitry is configured to control, in performing the reproduction process, the light source to emit the illumination light with the same light amount as the light amount stored in the memory.

10. The medical observation apparatus according to claim 1, wherein
the camera includes an image sensor configured to capture the object image under an imaging condition designated by the control circuitry,
the memory is configured to store the imaging condition designated by the control circuitry, and
the control circuitry is configured to control, in performing the reproduction process, the image sensor to capture the object image under the same imaging condition as the imaging condition stored in the memory.

11. The medical observation apparatus according to claim 2, wherein the control circuitry is configured to control, in performing the reproduction process, a notification unit to notify of movement information indicating a movement direction of the camera based on the position of the camera stored in the memory and the position of the camera currently detected by the position detector.

12. The medical observation apparatus according to claim 1, wherein
the memory is configured to store a captured image obtained by imaging of the camera, and
the control circuitry is configured to correct, in performing the reproduction process, the position of the camera stored in the memory based on the captured image stored in the memory and a captured image currently obtained by imaging of the camera.

13. The medical observation apparatus according to claim 2, wherein
the position detector is provided to each of at least two shafts among the plurality of shafts, configured to detect a rotation angle of the camera rotating about each of the at least two shafts,
the memory is configured to store, as the storage position of the camera, the rotation angle of the camera rotating about each of the at least two shafts detected by the position detector,
the brake is provided to each of the at least two shafts, and
the control circuitry is configured to perform the reproduction process for switching the brake to the permission state, and thereafter switch the brake from the permission state to the restriction state for each shaft at which a rotation angle matches with the rotation angle of the storage position stored in the memory by operating the support according to the external force applied to the support by the operator.

14. A medical observation system omprising:
a camera configured to capture an object image of an observation target;
a support configured to support the camera so as to be rotatable about a plurality of mutually-different shafts;

a memory configured to store a storage position of the camera;

a brake configured to switch between: a permission state for permitting the camera to rotate about at least one of the plurality of shafts; and a restriction state for restricting the rotation;

a control circuitry configured to perform a reproduction process for switching the brake to the permission state, and thereafter switching the brake from the permission state to the restriction state when the support is operated according to an external force applied to the support by an operator and the camera is located at the storage position of the camera stored in the memory; and a display device configured to display a captured image obtained by imaging of the camera.

15. The medical observation system according to claim 14, wherein at least two shafts of the plurality of shafts are switched to the restriction state sequentially.

16. The medical observation apparatus according to claim 13, wherein the at least two shafts are passive shafts configured to passively rotate the camera about the shaft according to the external force applied to the support by the operator.

17. The medical observation apparatus according to claim 1, wherein at least two shafts of the plurality of shafts are switched to the restriction state sequentially.

18. The medical observation apparatus according to claim 1, wherein each of the plurality of shafts are passive shafts.

19. The medical observation apparatus according to claim 1, wherein the plurality of shafts includes only one active shaft configured to actively rotate the camera about the shaft with a power of an actuator.

20. A medical observation apparatus comprising:

a memory configured to store a storage position of a camera supported by a support to be rotatable about a plurality of mutually-different shafts; and control circuitry configured to perform a reproduction process for switching a brake to a permission state for permitting the camera to rotate around at least one of the plurality of shafts, and thereafter switching the brake from the permission state to a restriction state for restricting the rotation when the support is operated according to an external force applied to the support by an operator and the camera is located at the storage position stored in the memory.

* * * * *